(12) United States Patent
Kang et al.

(10) Patent No.: US 12,127,841 B2
(45) Date of Patent: Oct. 29, 2024

(54) UPPER LIMB MULTI-JOINT IMPEDANCE MEASUREMENT METHOD AND APPARATUS USING THE SAME

(71) Applicant: Ulsan National Institute of Science and Technology, Ulsan (KR)

(72) Inventors: Sang Hoon Kang, Ulsan (KR); Sung Shin Kim, Ulsan (KR); Hyunah Kang, Ulsan (KR)

(73) Assignee: Ulsan National Institute of Science and Technology, Ulsan (KR)

( * ) Notice: Subject to any disclaimer, the term of this patent is extended or adjusted under 35 U.S.C. 154(b) by 270 days.

(21) Appl. No.: 15/716,536

(22) Filed: Sep. 27, 2017

(65) Prior Publication Data
US 2018/0085016 A1 Mar. 29, 2018

(30) Foreign Application Priority Data
Sep. 29, 2016 (KR) .................. 10-2016-0125453

(51) Int. Cl.
*A61B 5/24* (2021.01)
*A61B 5/00* (2006.01)
(Continued)

(52) U.S. Cl.
CPC ................ *A61B 5/24* (2021.01); *A61B 5/053* (2013.01); *A61B 5/1107* (2013.01);
(Continued)

(58) Field of Classification Search
CPC ....... A61B 5/4528; A61B 5/4585; A61B 5/45; A61B 5/4519; A61B 5/4533;
(Continued)

(56) References Cited

U.S. PATENT DOCUMENTS

2005/0085747 A1* 4/2005 Wilkinson ............. A61B 5/442
600/587
2008/0242521 A1* 10/2008 Einav ................. A63B 71/0009
482/110

(Continued)

FOREIGN PATENT DOCUMENTS

JP 10-094524 4/1998
KR 10-1600850 3/2016

*Primary Examiner* — Carrie R Dorna
*Assistant Examiner* — Karen E Toth

(57) ABSTRACT

The present disclosure relates to an upper limb multi-joint impedance measurement method and an apparatus using the same. An upper limb multi-joint impedance measurement apparatus includes an upper limb end connector connected to an end of an upper limb of a subject, a driver configured to drive the upper limb end connector so that the upper limb end connector applies perturbations to the end of the upper limb of the subject, a measurement controller configured to provide the driver with a control signal for the perturbations, a force sensor configured to detect a magnitude of a perturbation force applied to the end of the upper limb of the subject by the upper limb end connector, a position sensor configured to detect a variation of a position of the upper limb end connector according to the applied perturbations, an impedance calculator configured to calculate a mechanical impedance of the upper limb of the subject by using force data and position data indicating the detected magnitude of the force and the detected variation of the position, and an impedance output unit configured to output an output signal indicating a value of the calculated mechanical impedance.

14 Claims, 5 Drawing Sheets

(51) Int. Cl.
    *A61B 5/01*         (2006.01)
    *A61B 5/053*       (2021.01)
    *A61B 5/11*         (2006.01)
    *A61B 5/389*       (2021.01)

(52) U.S. Cl.
    CPC .............. *A61B 5/6824* (2013.01); *A61B 5/01* (2013.01); *A61B 5/1124* (2013.01); *A61B 5/389* (2021.01); *A61B 5/7257* (2013.01)

(58) Field of Classification Search
    CPC ..... A61B 5/4538; A61B 5/4576; A61B 5/458; A61B 5/459; A61B 5/4523
    See application file for complete search history.

(56) References Cited

U.S. PATENT DOCUMENTS

| | | | | |
|---|---|---|---|---|
| 2008/0262372 | A1* | 10/2008 | Manto | A61B 5/0488 |
| | | | | 600/546 |
| 2011/0087128 | A1* | 4/2011 | Sakoda | A61B 5/0488 |
| | | | | 600/546 |
| 2013/0079841 | A1* | 3/2013 | Su | A61N 1/36007 |
| | | | | 607/41 |
| 2015/0057809 | A1* | 2/2015 | Deck | A61F 2/76 |
| | | | | 700/275 |
| 2016/0324436 | A1* | 11/2016 | Miyazaki | A61B 5/0488 |
| 2017/0042455 | A1* | 2/2017 | Ling | A61B 5/1121 |

\* cited by examiner

UPPER LIMB MULTI-JOINT IMPEDANCE MEASUREMENT METHOD AND APPARATUS USING THE SAME

RELATED APPLICATION

This application claims the benefit of priority of Korean Patent Application No. 10-2016-0125453, filed on Sep. 29, 2016, the contents of which are incorporated herein by reference in their entirety.

FIELD AND BACKGROUND OF THE INVENTION

The present disclosure relates to an upper limb multi-joint impedance measurement method and an apparatus using the same, and more particularly, to a method of measuring mechanical impedance of an upper limb multi-joint of a subject on the basis of force, positions, and biosignals, according to perturbations applied to an end of an upper limb of the subject, and an apparatus using the same.

Mechanical impedance of an upper limb multi-joint is required in order for the rehabilitation of the upper limb multi-joint. The mechanical impedance of the upper limb multi-joint/degrees-of-freedom can be used to assist in diagnosing stiffness or the mechanical resistance against passive stretching of an upper limb of a patient. In addition, if the mechanical impedance of the upper limb multi-joint can be obtained accurately, rehabilitation programs can be prescribed and carried out according to the mechanical impedance. Also, an efficacy of rehabilitative training can be checked by frequently measuring the impedance at any time and comparing the impedance with premeasured impedance during the rehabilitative training, and the effect can be considered for preparation/adjustment/prescription of a subsequent rehabilitation program.

Conventional methods of measuring upper limb impedance are subjective methods that rely on experience of clinicians and hand feeling of the clinicians. However, the conventional methods have problems in that an impedance value may vary depending on a clinician who examined a patient, and thus reliability thereof is low. Also, the measured impedance has a qualitative value defined by an ordinal scale having about five steps, and thus it is difficult to measure a change in impedance unless the change is large.

Also, since a clinician moves the patient's upper limb with his or her hands to measure upper limb impedance, only impedance for one degree of freedom and a joint can be measured, and thus impedance for two or more degrees of freedom and joints or a coupled impedance between degrees of freedom and joints cannot be measured, which is a disadvantage of the subjective measurement method.

Impedance was measured using an upper limb rehabilitation robot or an industrial robot. Since such the robots are not designed solely for upper limb impedance measurement, the robots are very large in volume and difficult to install, in addition, serious problems in safety can occur in the case of industrial robots. Also, in terms of operation, the robots are complicated, and therefore, a robotics expert is required for clinical use. Further, the robots cannot be suitable for measuring upper limb impedance because the robots are unnecessarily large in size considering force perturbations or position perturbations, which are required for measuring the upper limb impedance.

Therefore, it is required to provide a technique relating to an apparatus capable of measuring impedance of multiple degrees of freedom and multiple joints of an upper limb, which is easy to manipulate and use with a size suitable for clinical use, and a method using the same.

PRIOR ART

Disclosure 1: Korean Patent Registration No. 10-1600850.

SUMMARY OF THE INVENTION

The present disclosure is directed to providing a method and an apparatus for easily measuring multi-joint impedance of an upper limb.

The technical objectives of the present disclosure are not limited to the above-described technical objectives, and other technical objectives, which are not described herein, may be clearly understood by those skilled in the art from the following description.

According to one aspect of the present disclosure, there is provided an upper limb multi-joint impedance measurement apparatus including: an upper limb end connector connected to an end of an upper limb of a subject; a driver configured to drive the upper limb end connector so that the upper limb end connector applies perturbations to the end of the upper limb of the subject, a measurement controller configured to provide the driver with a control signal for the perturbations; a force sensor configured to detect a magnitude of a perturbation force applied to the end of the upper limb of the subject by the upper limb end connector; a position sensor configured to detect a variation of a position of the upper limb end connector according to the applied perturbations; an impedance calculator configured to calculate a mechanical impedance of the upper limb of the subject by using force data and position data indicating the detected magnitude of the force and the detected variation of the position; and an impedance output unit configured to output an output signal indicating a value of the calculated mechanical impedance.

The upper limb end connector may include a part connected to the end of the upper limb of the subject and gripped by the subject.

The perturbations may include at least one of a force variation and a positional variation applied to the end of the upper limb by the upper limb end connector in at least one direction of x-axis direction, y-axis direction and z-axis direction.

The upper limb multi-joint impedance measurement apparatus may further include a biosignal sensor attached to the upper limb of the subject to detect a biosignal of the subject, wherein the impedance calculator may filter the force data or the position data on the basis of the detected biosignal.

The biosignal may include at least one of an electromyography (EMG) signal, a pulse, and a body temperature of the subject.

The biosignal sensor may include an inertial measurement unit (IMU) sensor configured to detect a relative position of the upper limb.

The impedance calculator may transform the force data and the position data into a frequency domain, calculate a transfer function under a condition in which the position data transformed into the frequency domain is set as input and the force data transformed into the frequency domain is set as output, and derive the mechanical impedance using the calculated transfer function The impedance output unit may include at least one selected from the group consisting of a display, an audio output device, and a printer.

According to another aspect of the present disclosure, there is provided an upper limb multi-joint impedance measurement method includes: applying, by an upper limb end connector driven by a driver, perturbations to an end of an upper limb of a subject; detecting a force of the upper limb end connector, which is applied to the end of the upper limb of the subject, while the perturbations are applied to the end of the upper limb; detecting a position of the upper limb end connector while the perturbations are applied to the end of the upper limb; calculating mechanical impedance of the upper limb of the subject on the basis of force data and position data respectively indicating the detected force and detected position; and outputting the calculated mechanical impedance.

The applying of the perturbation may include applying, by the upper limb connector, the force or the position to the end of the upper limb in any one direction of an x-axis direction, a y-axis direction, and a z-axis direction.

After the applying of the perturbations, the upper limb multi-joint impedance measurement method may further include detecting a bio signal of the subject while the perturbations are applied to the end of the upper limb After the detecting of the biosignal, the upper limb multi-joint impedance measurement method may further include restarting the measurement from the beginning when the EMG signal indicates a voluntary reaction signal, wherein the biosignal may include an electromyography signal (EMG) of the subject.

The calculating of the mechanical impedance may include: transforming the force data and the position data respectively indicating the detected force and the position, into a frequency domain; and calculating a transfer function under a condition in which the position data transformed into the frequency domain is set as input and the force data transformed into the frequency domain is set as output, and deriving the mechanical impedance using the calculated transfer function.

BRIEF DESCRIPTION OF THE SEVERAL VIEWS OF THE DRAWINGS

The above and other objects, features and advantages of the present disclosure will become more apparent to those of ordinary skill in the art by describing exemplary embodiments thereof in detail with reference to the accompanying drawings, in which.

DESCRIPTION OF SPECIFIC EMBODIMENTS OF THE INVENTION

Figure 1:
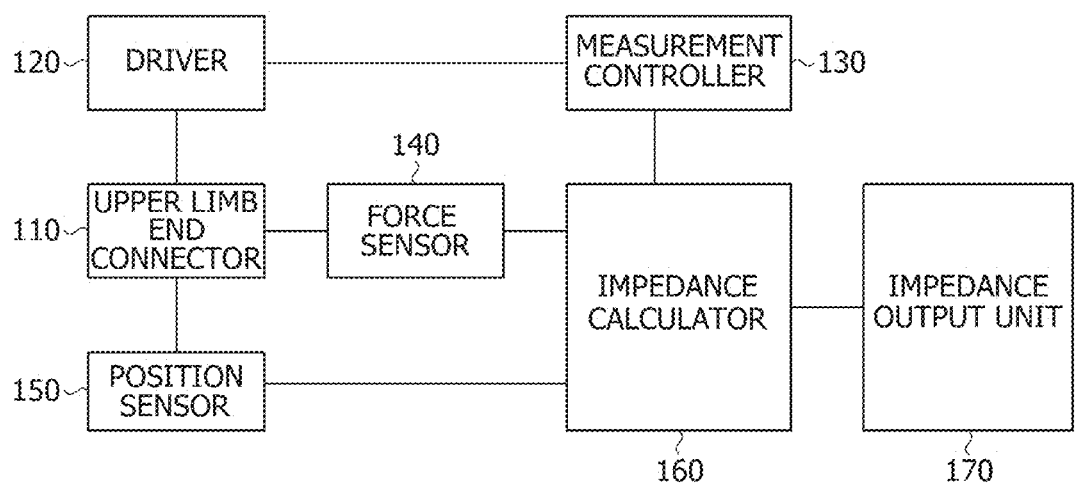
FIG. 1 is a block diagram of an upper limb multi-joint impedance measurement apparatus according to one embodiment of the present disclosure.

While the present disclosure is susceptible to various modifications and alternative forms, specific embodiments thereof are shown by way of example in the drawings and will herein be described in detail. However, it should be understood that this is not intended to limit the embodiments of the present disclosure with respect to any specific embodiment but includes all modifications, equivalents and alternatives falling within the spirit and scope of the embodiments is there.

Although terms including ordinal numbers such as first, second, or the like can be used to describe various components, the above components are not limited by the terms. The terms are only used to distinguish one component from another. For example, a second component may refer to a first component without departing from the scope of the embodiments, and similarly a first component may also refer to a second component. The term "and/or" includes any of a plurality of related entries or a combination of a plurality of related entries.

The terminology used in this application has been used merely to describe a specific embodiment and is not intended to limit the embodiments of the disclosure. The singular expression includes plural expressions unless the context clearly indicates otherwise. In the present application, the terms "including," "having," and the like is intended to specify that there are features, numbers, steps, actions, components, parts, or a combination thereof described on the specification, and do not preclude the presence or addition possibility of one or more other features or numbers, steps, operations, components, parts or combinations thereof.

In the description of the embodiment, in a case where it is stated that any element is formed as "above (on) or below (under)" of the other element, the term "above (on)" or "below (under)" includes all that two elements are in direct contact with each other or a plurality of other elements are formed indirectly between the two elements. In addition, when it is expressed as "above (on) or below (under)," not only the upward direction but also the downward direction with respect to one element can be included therein.

Hereinafter, embodiments will be described in detail with reference to the accompanying drawings, wherein like or corresponding elements are denoted by the same reference numerals, and redundant descriptions thereof will be omitted.

FIGS. 1 to 7 clearly illustrate only main parts in order to conceptually and clearly understand the present disclosure and, as a result, the drawings may be variously modified and the scope of the present disclosure is not limited to specific shapes shown in the drawings.

FIG. 1 is a block diagram of an upper limb multi-joint impedance measurement apparatus according to one embodiment of the present disclosure. A configuration of an upper limb multi-joint impedance measurement apparatus 100 according to one embodiment of the present disclosure will be described in detail with reference to FIG. 1.

The upper limb multi-joint impedance measurement apparatus 100 may include an upper limb end connector 110, a driver 120, a measurement controller 130, a force sensor 140, a position sensor 150, an impedance calculator 160, and an impedance output unit 170.

The upper limb end connector 110 is of a rod-like structure, and is a section which will be connected to an end of an upper limb of a subject. The upper limb end connector 110 may have a part that the subject may grip. For example, the part which the subject may grip may have a handle shape. By connecting the upper limb end connector 110 to the end of the upper limb of the subject to be measured, a preparation for measurement of impedance of an upper limb multi-joint may be completed. For example, the subject may attach the upper limb end connector 110 to his or her upper limb.

The driver 120 may drive the upper limb end connector 110. The driver 120 may have a motor connected to the upper limb end connector. The driver 120 may precisely drive the upper limb end connector 110 using the motor. The driver 120 may drive the upper limb end connector 110 so that perturbations are applied to an end of an upper limb in at least one direction of an x-axis direction, a y-axis direction, and a z-axis direction.

The measurement controller 130 may provide the driver 120 with a control command so that the upper limb end connector 110 applies perturbations to the end of the upper limb of the subject. For example, the measurement controller 130 may provide the driver 120 with a control command so that the upper limb end connector 110 applies perturbations associated with a position having random translational motion of up to 2 cm in at least one direction of the three-dimensional x, y and z axes to the end of the upper limb.

In a conventional upper limb multi-joint impedance measurement apparatus, impedance was measured by simply modeling the upper limb impedance into a second order linear system (mass-damper-spring). Also, in the conventional upper limb multi-joint impedance measurement apparatus, only an impedance value of an upper limb multi-joint on the two-dimensional horizontal plane may be estimated, and therefore, the impedance value is not accurately extracted due to assumption that an upper limb is the same as that made by the above described second order system.

However, since the present disclosure estimates three-dimensional impedance using perturbations in three dimensions, limitations caused by estimating only two-dimensional mechanical impedance of an upper limb on a horizontal plane has been eliminated. Also, since the three-dimensional impedance instead of the two-dimensional impedance is estimated, the resultants may be comprehensively derived.

Also, in the conventional upper limb multi-joint impedance measurement apparatus, perturbations are applied by pushing or pulling a subject in various directions in random order while the measuring apparatus moves a predetermined path. Experiment using the above method takes long time because it is necessary to experiment repeatedly on the same path for a large number of times to obtain all necessary data. Also, an amount of information in the data to be obtained is limited because the upper limb impedance may not be obtained in all frequency ranges of interest. On the other hand, since the apparatus according to the embodiment estimates impedance by applying perturbations in the form of unpredictable low-frequency filtered white noise in all three dimensions, impedance characteristics in all the frequency regions of interest are determined. In addition, since a time for applying the perturbations is shorter than that of the conventional apparatus, the apparatus according to the embodiment is efficient.

In addition, the perturbations in the form of unpredictable low frequency filtered white noise may minimize an amount of meaningless data, so the amount of meaningless data may be minimized.

The force sensor 140 is connected to the upper limb end connector 110 and may detect a magnitude of a force that is applied to the end of the upper limb through the upper limb end connector 110 while the upper limb end connector 110 is applying perturbations to the end of the upper limb by the operation of the driver 120. The force sensor 140 may have a pressure sensor. The force sensor 140 may output force data that indicates a magnitude and direction of the force detected by the upper limb end connector 110.

The position sensor 150 is connected to the upper limb end connector 110 and may detect a variation of a position of the upper limb end connector 110 while the upper limb end connector 110 is applying the perturbations to the end of the upper limb by the operation of the driver 120. The position sensor 150 may have one component selected from the group consisting of an encoder, a potentiometer, a resolver, an ultrasonic sensor, a laser sensor, an inertial measurement unit (IMU) sensor, and a motion capture camera to detect the variation of the position of the upper limb end connector 110. The position sensor 150 may output position data including information on the detected variation of the position of the upper limb end connector 110.

A method of deriving impedance using the impedance calculator 160 according to the embodiment of the present disclosure will be described with reference to FIG. 3.

The impedance calculator 160 may provide the measurement controller 130 with a measurement start signal and calculate mechanical impedance of an upper limb multi-joint (hereinafter, referred to as "upper limb impedance") of a subject using force data and position data respectively output from the force sensor 140 and the position sensor 150.

In order to calculate upper limb impedance, the impedance calculator 160 may use a method of estimating a system through force and displacement data measured when perturbations are applied to the system. For example, as shown in the following formula, a transfer function matrix ($Z_{xx}$ to $Z_{zz}$) may be calculated by using displacement data ($\Delta X$, $\Delta Y$, and $\Delta Z$) as input and force data ($F_x$, $F_y$, and $F_z$) as output, and the calculated transfer function matrix is mechanical impedance.

$$\begin{bmatrix} F_x \\ F_y \\ F_z \end{bmatrix} = \begin{bmatrix} Z_{xx} & Z_{xy} & Z_{xz} \\ Z_{yx} & Z_{yy} & Z_{yz} \\ Z_{zx} & Z_{zy} & Z_{zz} \end{bmatrix} \begin{bmatrix} \Delta X \\ \Delta Y \\ \Delta Z \end{bmatrix}$$

The force data and the position data may be data including minutely change values over time. The impedance calculator 160 may perform signal processing on the force data and the position data to calculate the upper limb impedance. According to one embodiment of the present disclosure, the impedance calculator 160 transforms the force data and the position data into a frequency domain. The impedance calculator 160 may transform the force data and the position data into the frequency domain using a Fourier transform, but this is for exemplary purposes only, and the transformation is not limited thereto.

The impedance calculator 160 calculates a transfer function under a condition in which the position data transformed into the frequency domain is set as input and the force data transformed into the frequency domain is set as output. The impedance calculator 160 may derive upper limb impedance using the calculated transfer function.

For example, when position data of the frequency domain is represented by Xh and force data of the frequency domain is represented by Fh, a transfer function Zh may be defined as follows. When the transfer function Zh is calculated using the following formula, the calculated transfer function Zh becomes upper limb impedance.

$$F_h = Z_h x_h$$

$$\begin{bmatrix} F_x \\ F_y \\ F_z \end{bmatrix} = \begin{bmatrix} z_{11} & z_{12} & z_{13} \\ z_{21} & z_{22} & z_{23} \\ z_{31} & z_{32} & z_{33} \end{bmatrix} \begin{bmatrix} x \\ y \\ z \end{bmatrix}$$

The calculation of the transfer function Zh in the above formula should be obvious to those of ordinary skill in the art, and a detailed description thereof will be omitted.

Referring back to FIG. 1, the impedance output unit 170 may output upper limb impedance calculated by the impedance calculator 160. The impedance output unit 170 may have at least one device selected from the group consisting of a display, an audio output device, and a printer. For example, when the impedance output unit 170 has a display, the calculated upper limb impedance may be displayed on the display.

Figure 2:
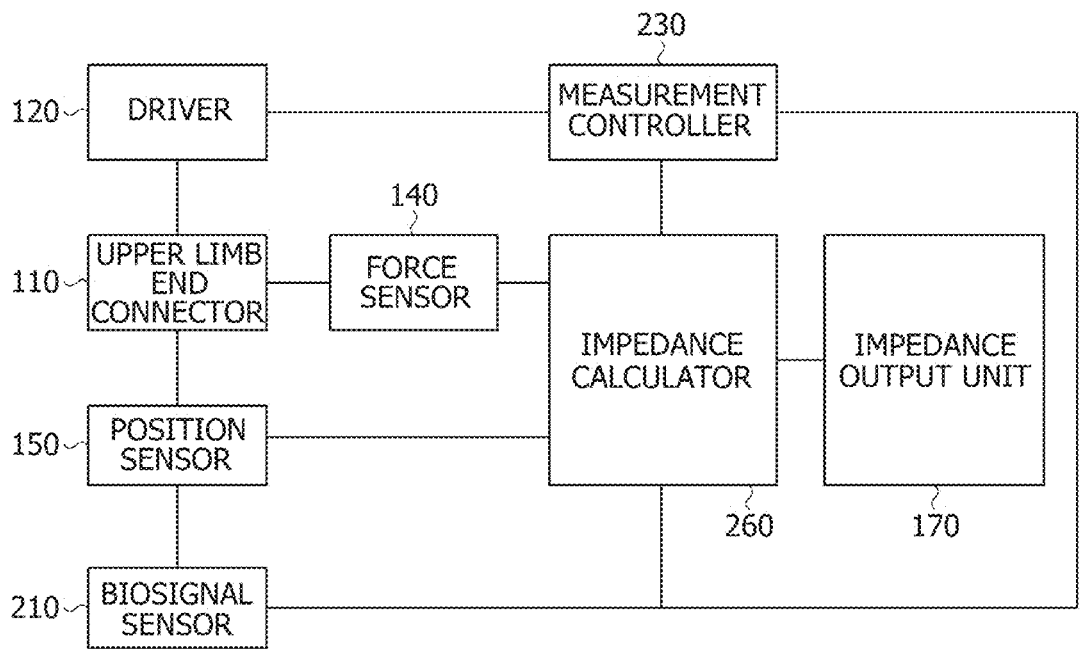
FIG. 2 is a block diagram of an upper limb multi-joint impedance measurement apparatus according to another embodiment of the present disclosure.

FIG. 2 is a block diagram of an upper limb multi-joint impedance measurement apparatus according to another embodiment of the present disclosure. Referring to FIG. 2, a configuration of an upper limb impedance measurement apparatus 200 according to another embodiment of the present disclosure will be described in detail.

The upper limb impedance measurement apparatus 200 according to another embodiment of the present disclosure may further include a biosignal sensor 210 compared with the upper limb impedance measurement apparatus 100 according to one embodiment. Since components, which have the same reference numerals as the components of the upper limb impedance measurement apparatus 100 in a configuration of the upper limb impedance measurement apparatus 200, are the same as those of the upper limb impedance measurement apparatus 100, descriptions thereof will be omitted to prevent overlapping descriptions.

The biosignal sensor 210 may be attached to an upper limb of a subject to detect a biosignal of the subject. The biosignal may include at least one of an electromyography (EMG) signal, a pulse, and a body temperature of the subject. The biosignal sensor 210 may output biosignal data that indicates the detected biosignal.

The biosignal sensor 210 may have an inertial measurement unit (IMU) sensor configured to detect a relative position of the upper limb. The biosignal sensor 210 may output biometric signal data including data detected by the IMU sensor.

An impedance calculator 260 may filter information of the measured data through the force sensor and the position sensor on the basis of the biosignal data output from the biosignal sensor 210.

For example, when the impedance calculator 260 checks a body condition of the subject on the basis of an electromyography signal (EMG) included in the biosignal and determines that a voluntary reaction signal is included in the checked result, the impedance calculator 260 excludes data measured in the presence of a voluntary movement.

Because accurate measurement data is not made when a voluntary reaction exists, impedance may not be accurately calculated. Therefore, by filtering data according to the voluntary movement, the impedance can be more accurate.

In addition, by using the biosignal data, the impedance calculator 260 may determine a relationship between the calculated upper limb impedance and the biosignal data output. For example, a correlation between an EMG signal level included in the biosignal data and the impedance value may be checked using a statistical method.

Figure 4:
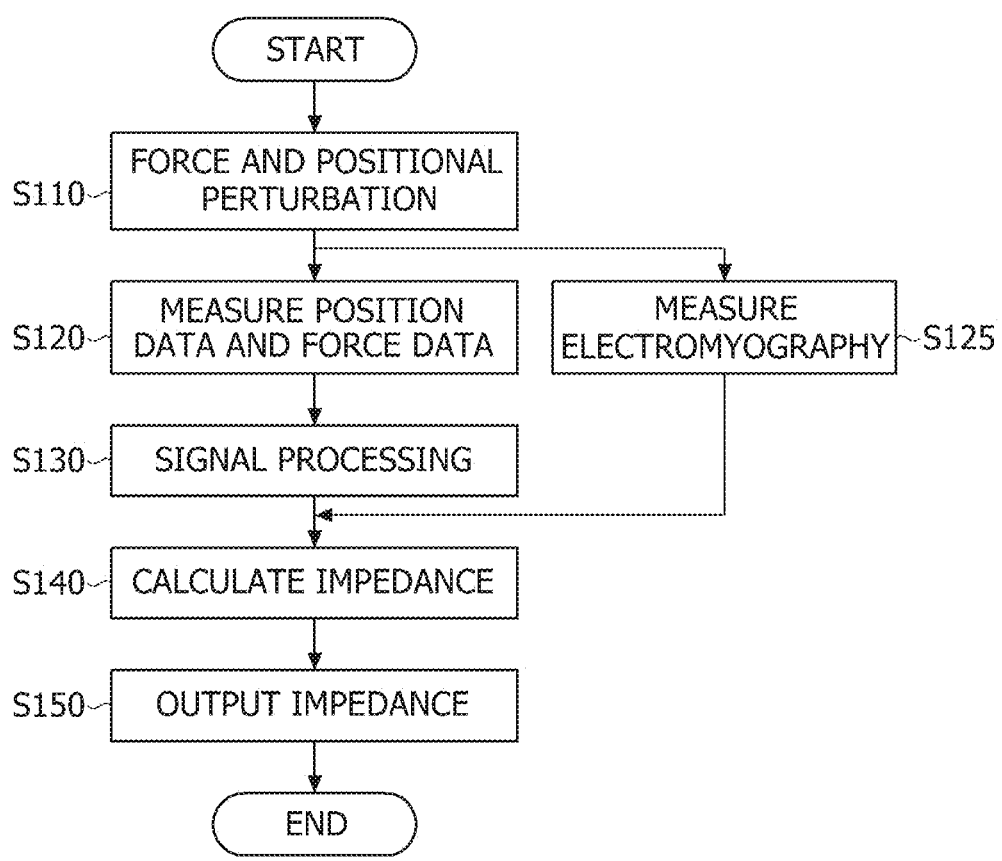
FIG. 4 is a flowchart illustrating a method of measuring impedance of an upper limb multi-joint according to one embodiment of the present disclosure.

FIG. 4 is a flowchart illustrating a method of measuring impedance of an upper limb multi-joint according to one embodiment of the present disclosure. The method of measuring impedance of an upper limb multi-joint according to one embodiment of the present disclosure will be described in detail with reference to FIG. 4.

An end of an upper limb of a subject is connected to the upper limb end connector 110, and the measurement controller 130 provides a control signal to the driver 120 so that the upper limb end connector 110 applies perturbations to the end of the upper limb (S110).

For example, when the end of the upper limb of the subject is connected to the upper limb end connector 110 and a start signal is provided to the upper limb multi-joint impedance measurement apparatus 100, the measurement controller 130 provides a control signal to the driver 120. The driver 120 may precisely drive the upper limb end connector 110 in at least one direction of x-axis, y-axis, and z-axis directions.

While the upper limb end connector 110 is moving, the force sensor 140 detects a force applied by the upper limb end connector to the end of the upper limb, and the position sensor 150 detects a position of the upper limb end connector 110 (S120).

The impedance calculator 160 may perform signal processing on the force data and the position data (S130). The force data and the position data may be data including minutely change values over time. The impedance calculator 160 may transform the force data and the position data into a frequency domain.

The impedance calculator 160 calculates upper limb impedance based on the force data transformed into the frequency domain and the position data transformed into the frequency domain (S140). The impedance calculator 160 calculates the transfer function in a condition where the position data transformed into the frequency domain is set as input and the force data transformed into the frequency domain is set as output. The impedance calculator 160 may derive upper limb impedance using the calculated transfer function.

An impedance output unit 170 outputs the upper limb impedance (S150). When the impedance output unit 170 has a display, the upper limb impedance may be displayed on the display.

Figure 5:
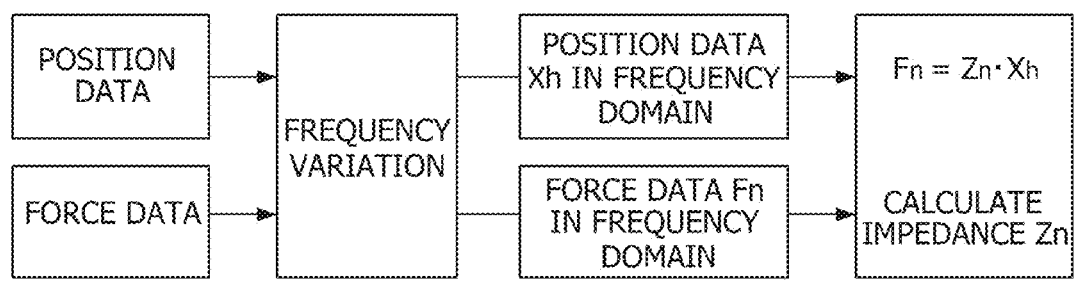
FIG. 5 is a flowchart illustrating a method of measuring impedance of an upper limb multi-joint according to another embodiment of the present disclosure.

FIG. 5 is a flowchart illustrating a method of measuring impedance of an upper limb multi-joint according to another embodiment of the present disclosure. The method of measuring impedance of an upper limb multi-joint according to another embodiment of the present disclosure will be described in detail with reference to FIG. 5.

Figure 3:
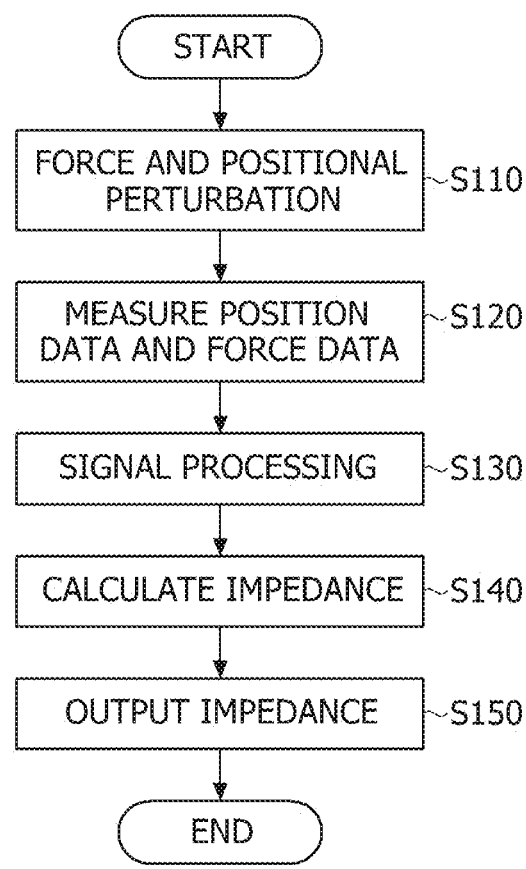
FIG. 3 is a schematic view illustrating a method of measuring impedance of an upper limb multi-joint using an upper limb multi-joint impedance measurement apparatus according to another embodiment of the present disclosure.

Referring to FIGS. 3 and 5, the method of measuring upper limb multi-joint impedance according to another embodiment is the same as that according to one embodiment except that an EMG signal is additionally measured (S125) after perturbations are applied (S110) in the method of measuring impedance of upper limb multi-joint according to one embodiment. Accordingly, since operations of another embodiment having the same reference symbols as those of one embodiment are the same as those of one embodiment, a description thereof will be omitted to prevent overlapping descriptions.

In the method of measuring impedance of upper limb multi-joint according to another embodiment of the present disclosure, an EMG signal is measured on an upper limb of a subject while the upper limb end connector 110 is applying perturbations to the upper limb (S125). When a voluntary reaction signal is included in the measured EMG signal, the measurement controller 130 may provide a control signal to the driver 120 so that measurement may be restarted from the beginning.

Also, the impedance calculator 260 may derive upper limb impedance on the basis of the force data, the position data, and the measured EMG signal. Also, the impedance calculator 260 may derive a relationship between the calculated impedance value and the measured EMG signal.

Figure 6:
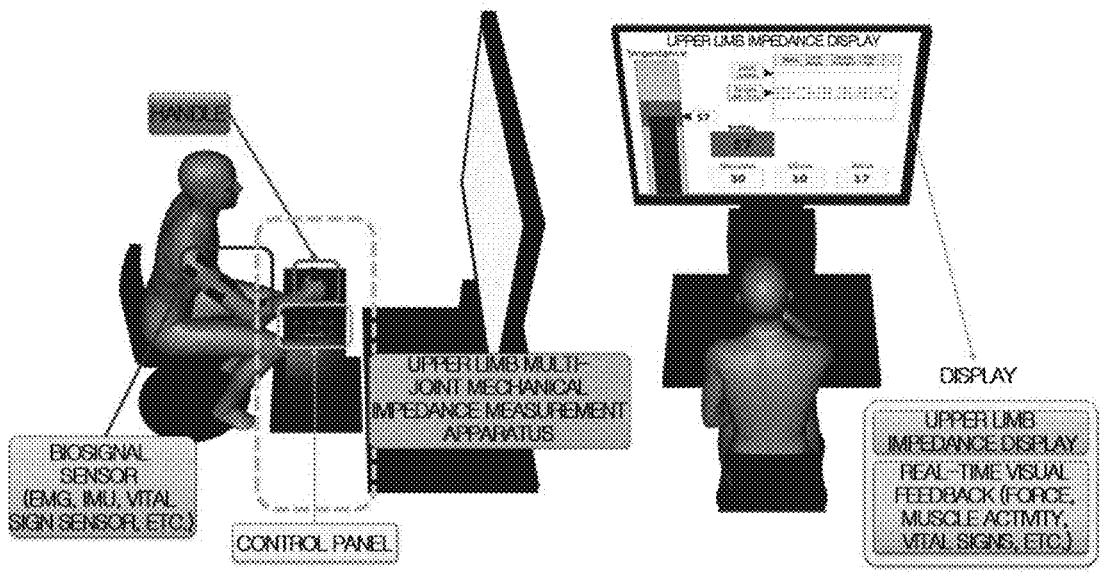
FIG. 6 is a conceptual view illustrating the use of an upper limb multi-joint impedance measurement apparatus according to another embodiment of the present disclosure.

FIG. 6 is a conceptual view illustrating the use of an upper limb multi-joint impedance measurement apparatus according to another embodiment of the present disclosure. Referring to FIG. 6, a subject may sit in front of the upper limb multi-joint impedance measurement apparatus 200, connect an end of his or her upper limb to the upper limb end connector 110, and operate a control panel to start measuring his or her upper limb impedance. The control panel is provided so that both a measurer (clinician) and the subject can operate. The upper limb impedance is calculated using a magnitude of a force applied to the end of the upper limb by an upper limb end connector, a variation of a position of the end of the upper limb, and data of the subject collected by a biosignal sensor, and the calculated upper limb impedance may be displayed on a display of the impedance output unit.

Figure 7:
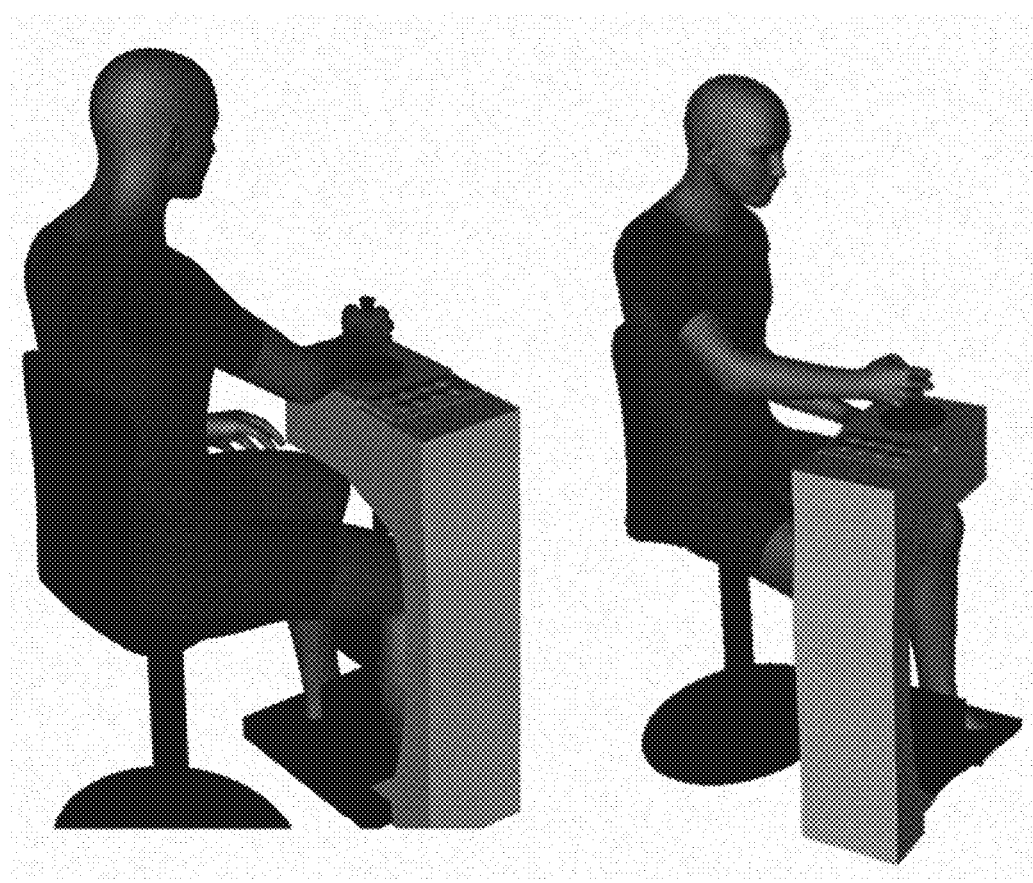
FIG. 7 is a view illustrating an example of using an upper limb multi-joint impedance measurement apparatus according to another embodiment of the present disclosure.

FIG. 7 is a view illustrating an example of using an upper limb multi-joint impedance measurement apparatus according to another embodiment of the present disclosure.

Referring to FIG. 7, a subject may sit in front of the upper limb multi-joint impedance measurement apparatus 200, connect an end of his or her upper limb to the upper limb end connector 110, and measure his or her upper limb impedance.

According to the above-described present disclosure, a subject attaches an upper limb end connector of an upper limb multi-joint impedance measurement apparatus to an end of his or her upper limb and operates the apparatus so that perturbations are applied to the end of his or her upper limb through the upper limb end connector, thereby effectively measuring impedance of upper limb multi-joint. The various advantageous benefits and effects of the present disclosure are not limited to the contents described above and may be understood more easily in the course of explaining specific embodiments of the present disclosure.

The above-described embodiments are merely illustrative of the technical idea of the present disclosure, and those having ordinary skill in the technical field to which the present disclosure belongs may make various modifications, changes, and substitutions without departing from the essential characteristics of the present disclosure. Therefore, the embodiments disclosed in the present disclosure and the accompanying drawings are intended to illustrate rather than limit the technical spirit of the present disclosure, and the scope of the technical idea of the present disclosure is not limited by these embodiments and the accompanying drawings. The scope of protection of the present disclosure should be interpreted by the following claims, and all technical ideas within the equivalent scope are to be interpreted as being included in the scope of the present disclosure.

What is claimed is:

1. An upper limb multi-joint impedance measurement apparatus comprising:
a platform configured to be disposed in an elevated position above ground;
a handle mounted on the platform and configured in size and shape for being gripped by a subject so as to be thereby connected to an end of an upper limb of the subject;
a driver coupled to the handle and configured to drive the handle to apply perturbations to the end of the upper limb of the subject in response to the handle being gripped by the subject, the perturbations comprise at least one of a force variation and a positional variation in at least one direction of x-axis direction, y-axis direction and z-axis direction;
a measurement controller coupled to the driver and configured to provide the driver with a control signal for the perturbations;
a control panel integrated in the platform and configured to be operated by the subject for initiating operation of the measurement controller;
a force sensor coupled to the handle and configured to detect a magnitude and direction of a force applied by the handle to the end of the upper limb of the subject in response to the perturbations being applied by the handle to the end of the upper limb of the subject by operation of the driver;
a position sensor coupled to the handle and configured to detect a variation of a position of the handle in response to the perturbations being applied by the handle to the end of the upper limb of the subject by operation of the driver;
a processing circuitry configured to analyze force data indicating the magnitude and direction of force detected by the force sensor and position data indicating the variation of the position detected by the position sensor in order to obtain at least one value of a mechanical impedance of the upper limb of the subject, the at least one value of the mechanical impedance is derived using a transfer function where the position data is set as an input of the transfer function and the force data is set as an output of the transfer function; and
an output unit configured to provide real-time feedback according to the at least one value of the mechanical impedance of the upper limb of the subject by outputting at least one of a visual and an audio signal.

2. The upper limb multi-joint impedance measurement apparatus of claim 1, further comprising at least one biological sensor attachable to the upper limb of the subject and configured to detect at least one biological signal of the subject in response to the perturbations being applied by the handle to the end of the upper limb of the subject by operation of the driver.

3. The upper limb multi-joint impedance measurement apparatus of claim 2, wherein the at least one biological signal comprises at least one of a pulse, and a body temperature of the subject.

4. The upper limb multi-joint impedance measurement apparatus of claim 2, wherein the at least one biological sensor comprises an inertial measurement unit (IMU) configured to detect a relative position of the upper limb of the subject.

5. The upper limb multi-joint impedance measurement apparatus of claim 2, wherein the at least one biological signal comprises an electromyography (EMG) signal.

6. The upper limb multi-joint impedance measurement apparatus of claim 1, wherein the processing circuitry is further configured to transform the force data and the position data into a frequency domain, wherein the position data transformed into the frequency domain is set as the input of the transfer function and the force data transformed into the frequency domain is set as the output of the transfer function.

7. The upper limb multi-joint impedance measurement apparatus of claim 1, wherein the perturbations comprise random positional variations along at least one of the x-axis, the y-axis, and the z-axis.

8. An upper limb multi-joint impedance measurement method comprising:
providing a subject with a handle mounted on a platform, wherein the platform is configured to be disposed in an elevated position above ground, and wherein the handle is configured in size and shape for being gripped by the subject so as to be thereby connected to an end of an upper limb of the subject;
in response to the handle being gripped by the subject, applying perturbations to the end of the upper limb of the subject by a driver coupled to the handle and configured to drive the handle to apply the perturbations, wherein the perturbations comprising at least one of a force variation and a positional variation in at least one direction of x-axis direction, y-axis direction and z-axis direction, wherein the driver is provided with a control signal for the perturbations by a measurement controller coupled to the driver, and wherein operation of the measurement controller is initiated by the subject operating a control panel integrated in the platform;
detecting by a force sensor coupled to the handle a magnitude and direction of a force applied by the handle to the end of the upper limb of the subject in response to the perturbations being applied by the handle to the end of the upper limb of the subject by operation of the driver;
detecting by a position sensor coupled to the handle a variation of a position of the handle in response to the perturbations being applied by the handle to the end of the upper limb of the subject by operation of the driver;
analyzing by a processing circuitry force data indicating the magnitude and direction of force detected by the force sensor and position data indicating the variation of the position detected by the position sensor in order to obtain at least one value of a mechanical impedance of the upper limb of the subject, the at least one value of the mechanical impedance is derived using a transfer function where the position data is set as an input of the transfer function and the force data is set as an output of the transfer function; and
providing by an output unit real-time feedback according to the at least one value of the mechanical impedance of the upper limb of the subject by outputting at least one of a visual and an audio signal.

9. The upper limb multi-joint impedance measurement method of claim 8, further comprising: detecting by at least one biological sensor attachable to the upper limb of the subject at least one biological signal of the subject in response to the perturbations being applied by the handle to the end of the upper limb of the subject by operation of the driver.

10. The upper limb multi-joint impedance measurement method of claim 9, wherein the at least one biological signal comprises at least one of a pulse, and a body temperature of the subject.

11. The upper limb multi-joint impedance measurement method of claim 9, wherein the at least one biological sensor comprises an inertial measurement unit (IMU) configured to detect a relative position of the upper limb of the subject.

12. The upper limb multi-joint impedance measurement method of claim 9, wherein the at least one biological signal comprises an electromyography (EMG) signal.

13. The upper limb multi-joint impedance measurement method of claim 8, further comprising transforming by the processing circuitry the force data and the position data into a frequency domain, wherein the position data transformed into the frequency domain is set as the input of the transfer function and the force data transformed into the frequency domain is set as the output of the transfer function.

14. The upper limb multi-joint impedance measurement method of claim 8, wherein the perturbations comprise random positional variations along at least one of the x-axis, the y-axis, and the z-axis.

* * * * *